US012745996B2

(12) United States Patent
Italiaie et al.

(10) Patent No.: US 12,745,996 B2
(45) Date of Patent: Sep. 29, 2026

(54) SURGICAL SYSTEM AND METHOD

(71) Applicant: Warsaw Orthopedic, Inc., Warsaw, IN (US)

(72) Inventors: Christel Italiaie, Memphis, TN (US); Bret Matthew Wilfong, Hernando, MS (US); Richard A. Hynes, Melbourne Beach, FL (US); Charles Hopkins Crawford, Prospect, KY (US); Roger Kirk Owens, Prospect, KY (US); Mladen Djurasovic, Louisville, KY (US); Jeffrey Lynn Gum, Pewee Valley, KY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 681 days.

(21) Appl. No.: 17/669,194

(22) Filed: Feb. 10, 2022

(65) Prior Publication Data

US 2023/0248347 A1 Aug. 10, 2023

(51) Int. Cl.
*A61B 17/02* (2006.01)
*A61B 17/68* (2006.01)

(52) U.S. Cl.
CPC ........ *A61B 17/025* (2013.01); *A61B 17/0206* (2013.01); *A61B 2017/0256* (2013.01); *A61B 2017/681* (2013.01)

(58) Field of Classification Search
CPC .... A61B 17/02; A61B 17/025; A61B 17/0206
See application file for complete search history.

(56) References Cited

U.S. PATENT DOCUMENTS

| | | | | |
|---|---|---|---|---|
| 5,984,867 | A * | 11/1999 | Deckman | A61B 17/0206 600/231 |
| 8,226,554 | B2 * | 7/2012 | McBride | A61B 17/0206 600/219 |
| 9,307,972 | B2 | 4/2016 | Lovell et al. | |
| 9,795,370 | B2 * | 10/2017 | O'Connell | A61B 17/02 |
| 10,499,897 | B2 | 12/2019 | Truckey | |
| 2005/0021040 | A1 | 1/2005 | Bertagnoli | |
| 2008/0177270 | A1 | 7/2008 | Sorrenti et al. | |
| 2010/0331849 | A1 * | 12/2010 | Riesinger | A61B 17/7077 606/90 |

(Continued)

FOREIGN PATENT DOCUMENTS

WO 2020219018 A1 10/2020

OTHER PUBLICATIONS

European Patent Office, 80298 Munich, Germany, Extended European Search Report, Application No. 22205024.7, Dated Jul. 10, 2023.

*Primary Examiner* — Christopher J Beccia
(74) *Attorney, Agent, or Firm* — Sorell, Lenna & Schmidt, LLP

(57) ABSTRACT

A surgical system includes a plurality of alternate engaging surfaces. A first member is connectable with an engaging surface such that the first member is interchangeable with the plurality of engaging surfaces. A second member is connectable with an engaging surface such that the second member is interchangeable with the plurality of engaging surfaces. The members are relatively movable to distract and/or compress vertebral tissue. Surgical instruments, constructs, implants and methods are disclosed.

20 Claims, 14 Drawing Sheets

(56) References Cited

U.S. PATENT DOCUMENTS

| | | | | |
|---|---|---|---|---|
| 2014/0024900 | A1* | 1/2014 | Capote | A61B 17/0206<br>600/214 |
| 2018/0110504 | A1* | 4/2018 | McAfee | A61F 2/4455 |
| 2020/0129168 | A1* | 4/2020 | Reitblat | A61B 17/025 |

* cited by examiner

SURGICAL SYSTEM AND METHOD

TECHNICAL FIELD

The present disclosure generally relates to medical devices for the treatment of spinal disorders, and more particularly to a surgical system and a method for treating of a spinal disorder.

BACKGROUND

Spinal disorders such as degenerative disc disease, disc herniation, osteoporosis, spondylolisthesis, stenosis, scoliosis, kyphosis and other curvature abnormalities, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, ligamentotaxy, corpectomy, discectomy, laminectomy, fusion, fixation and implantable prosthetics. Correction treatments used for positioning and alignment of vertebrae may employ spinal implants including spinal constructs and interbody devices for stabilization of a treated section of a spine. In some cases, the spinal implants may be manipulated with surgical instruments for compression and distraction of vertebrae. This disclosure describes an improvement over these prior technologies.

SUMMARY

In one embodiment, a surgical system is provided. The surgical system includes a plurality of alternate engaging surfaces. A first member is connectable with an engaging surface such that the first member is interchangeable with the plurality of engaging surfaces. A second member is connectable with an engaging surface such that the second member is interchangeable with the plurality of engaging surfaces. The members are relatively movable to distract and/or compress vertebral tissue. In some embodiments, surgical instruments, constructs, implants and methods are disclosed.

In one embodiment, the surgical system includes a longitudinal element and a plurality of alternate engaging surfaces. A first member is connected with the longitudinal element and is connectable with an engaging surface such that the first member is interchangeable with the plurality of engaging surfaces. A second member is connected with the longitudinal element and is connectable with an engaging surface such that the second member is interchangeable with the plurality of engaging surfaces. The members are relatively movable to distract and/or compress vertebral tissue.

In one embodiment, the surgical system includes a plurality of engaging surfaces. A first member is connectable with an engaging surface such that the first member is compatible with the plurality of engaging surfaces. A second member is connectable with an engaging surface such that the second member is compatible with the plurality of engaging surfaces. The engaging surfaces are selected for connection with the members such that the members are relatively movable to distract and/or compress vertebral tissue.

BRIEF DESCRIPTION OF THE DRAWINGS

The present disclosure will become more readily apparent from the specific description accompanied by the following drawings, in which.

DETAILED DESCRIPTION

Figure 1:
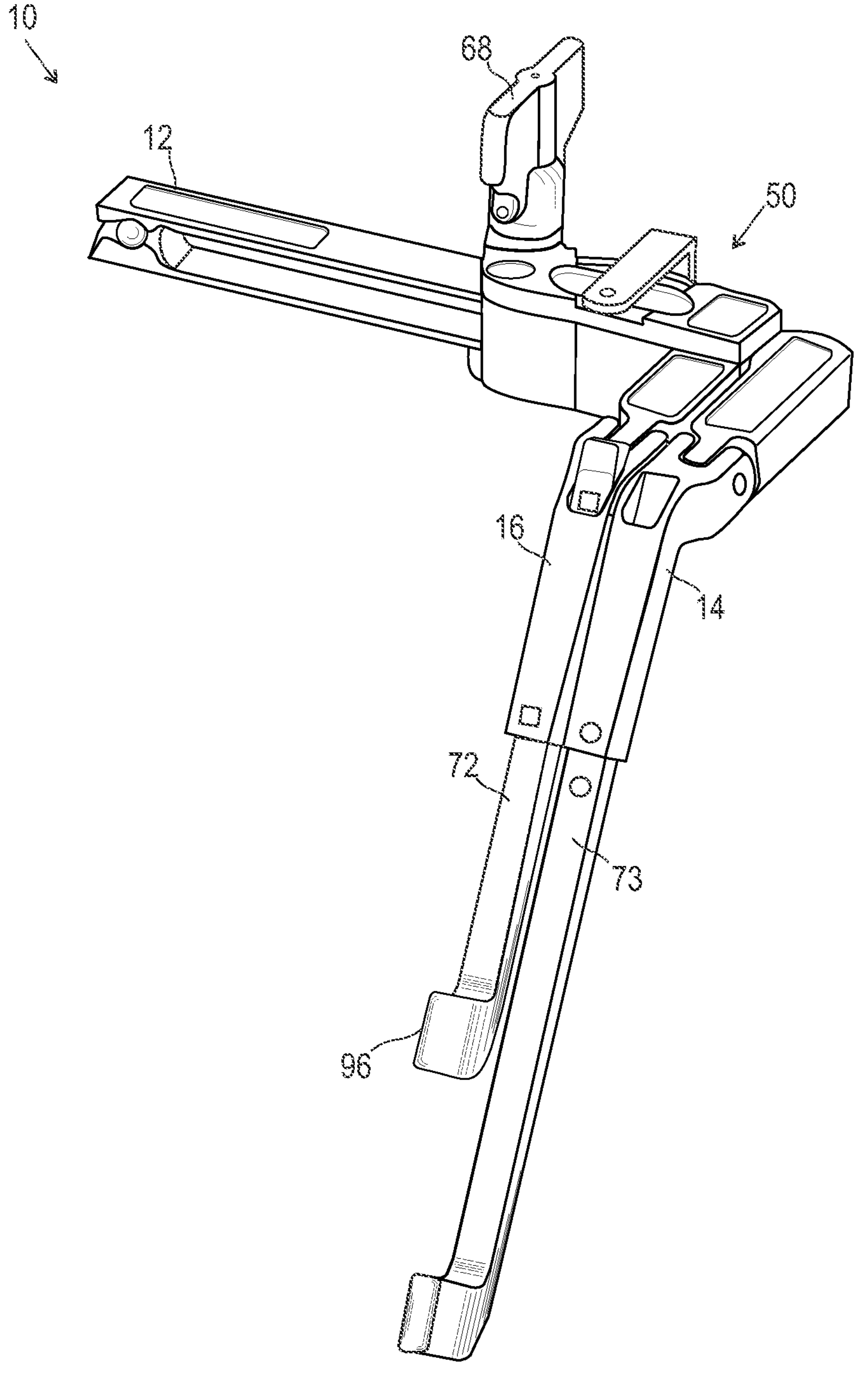
FIG. 1 is a perspective view of components of one embodiment of a surgical system in accordance with the principles of the present disclosure.

The exemplary embodiments of the system and related methods of use disclosed are discussed in terms of medical devices for the treatment of musculoskeletal disorders and more particularly, in terms of a surgical system and method for treating a spine disorder. In some embodiments, the present surgical system includes a surgical instrument including a distractor that allows vertebral manipulation during one or more surgical procedures, for example, correction, ligamentotaxy, corpectomy, discectomy, laminectomy, fusion, fixation, implantable prosthetics, facetectomy, disc preparation and/or interbody placement. In some embodiments, the present surgical system is configured for engagement with vertebral tissue, for example, spinous process, laminae and/or attachment to bone fasteners, including pedicle screws for parallel distraction and/or compression of the vertebral tissue.

In some embodiments, the present surgical system includes a modular spinal distraction system that consolidates stand-alone instrumentation into a single modular distraction platform that can be employed to distract vertebral tissue. In some embodiments, the present surgical system includes a surgical instrument, for example, a distractor rack and a plurality of legs. In some embodiments, the distractor rack and the plurality of legs are configured to create a cavity between adjacent vertebral bodies and/or multilevel vertebral bodies to provide space for a practitioner to perform a surgical procedure.

In some embodiments, the present surgical system includes a distractor including a distraction rack. In some embodiments, the distraction rack includes a frame and a pair of legs. In some embodiments, the frame is configured to drive the pair of legs apart or together to distract or compress vertebral tissue such that a gap is formed between vertebral bodies to provide space at a surgical site for a surgical procedure. In some embodiments, the pair of legs are variously configured for attachment to vertebral tissue, for example, the spinous process and/or the lamina tissue. In some embodiments, the pair of legs are variously configured for attachment to pedicle screws fixed with vertebral tissue. In some embodiments, the pair of legs include anatomic distractor legs configured for attachment to vertebral tissue including laminae and/or spinous process. In some embodiments, the anatomic distractor legs include an end including a textured surface configured for engagement with vertebral tissue. In some embodiments, the surface is textured to facilitate connection with a surface of vertebral tissue. In some embodiments, the pair of legs include shank based distractor legs configured for connection with a shank of a bone fastener, for example, a bone screw.

In some embodiments, the present surgical system includes a modular distraction rack configured to connect with a plurality of alternately configured distractor legs, each configured for engagement with selected vertebral tissue or pedicle screws fixed with vertebral tissue. In some embodiments, the distraction rack includes a pair of arms that each include a sleeve. In some embodiments, each leg is configured for connection with each sleeve. In some embodiments, an end of the leg includes a mating surface including a projection configured for mating connection with a mating surface including a groove defined from the sleeve. In some embodiments, the projection is square or circular shaped and matingly corresponds to a square or circular shaped groove. In some embodiments, the mating surfaces enable assembly of the surgical system. In some embodiments, the pair of legs are assembled on a back table in an operating room or in situ by positioning the pair of legs adjacent to respective anatomy/shanks and slidably engaging the sleeves with ends of the legs. In some embodiments, each leg includes a height that is configured for adjustment within the sleeves.

In some embodiments, the present distraction rack includes a spring loaded tab configured to prevent disassembly of components of the distraction rack including disassembly of a rack from a frame of the distraction rack. In some embodiments, the spring loaded tab is disposed on an end of the rack. In some embodiments, the distraction rack includes a spring loaded ball configured to prevent disassembly of the rack from the frame. In some embodiments, the sleeves of the distraction rack include a friction fit connection with portions of each of the legs to fix the legs with the sleeves. In some embodiments, the friction connection enables height adjustment of the pair of legs. In some embodiments, the pair of legs include a square profile and the sleeves include a square profile to facilitate a mating fixation, load transfer and/or modularity.

In some embodiments, the present surgical system is utilized with a method to correct spinal deformities. In some embodiments, the present surgical system is utilized with a method to treat degenerative spinal disorders and/or employed with transforaminal lumbar interbody fusion procedures. In some embodiments, the present surgical system is configured for utilization with a sagittal adjusting screw (SAS), a fixed axis screw (FAS) and/or a multi-axial screw (MAS). In some embodiments, the present surgical system comprises a single distractor to treat degenerative spinal disorders, for example, for disposal along a side of vertebrae oriented for decompression and/or interbody cage insertion.

In some embodiments, the present surgical system includes a surgical method including an interbody fusion, posterior lumbar interbody fusion (PLIF), transforaminal lumbar interbody fusion (TLIF) utilizing a minimally invasive surgical approach or a percutaneous approach. In some embodiments, the present surgical system includes segmental distraction to facilitate decompression, including final construct compression.

In some embodiments, one or all of the components of the surgical system are disposable, peel-pack, pre-packed sterile devices used with a spinal construct. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including posterior and/or posterior mid-line and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior."

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are disclosed. Reference is made to the exemplary embodiments of the present disclosure, which are illustrated in the accompanying figures. Turning to FIGS. 1-12, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaprolactone and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a minimally invasive procedure, including percutaneous techniques, mini-open and open surgical techniques to deliver and introduce instrumentation and/or components of spinal constructs at a surgical site within a patient body of a patient, for example, a section of a spine. In some embodiments, one or more of the components of surgical system 10 are configured for engagement with spinal constructs attached with vertebrae to manipulate tissue and/or correct a spinal disorder, as described herein. In some embodiments, surgical system 10 may be employed with surgical procedures, such as, for example, corpectomy, discectomy and/or fracture/trauma treatment and may include fusion and/or fixation that employ implants to restore the mechanical support function of vertebrae.

Surgical system 10 includes a longitudinal element including a distractor rack 12, as shown in FIG. 1. Rack 12 is configured for connection with a member, including a tubular arm 14 and a member including a tubular arm 16, as described herein, that are connectable to engaging surfaces, for example, a leg 72 and/or a leg 73 that are movable to distract and/or compress vertebral tissue. Arms 14, 16 are connectable with alternate engaging surfaces such that the engaging surfaces are interchangeable depending on the selected surgical treatment, surgical procedure, method and/or vertebral tissue at a surgical site, as described herein. In some embodiments, the engaging surface may include a blade, an arm, a paddle, and/or a hook. In some embodiments, arms 14, 16 are connectable with one or more engaging surfaces having the same or different configurations. In some embodiments, the engaging surface may be configured, oriented and/or disposed to contact, abut, engage, support, deform and/or penetrate tissue, one or more implants and/or surgical instrumentation. In some embodiments, the engaging surface may be employed with and/or include an insert, barrier, layer, coating and/or substrate.

Figure 3:
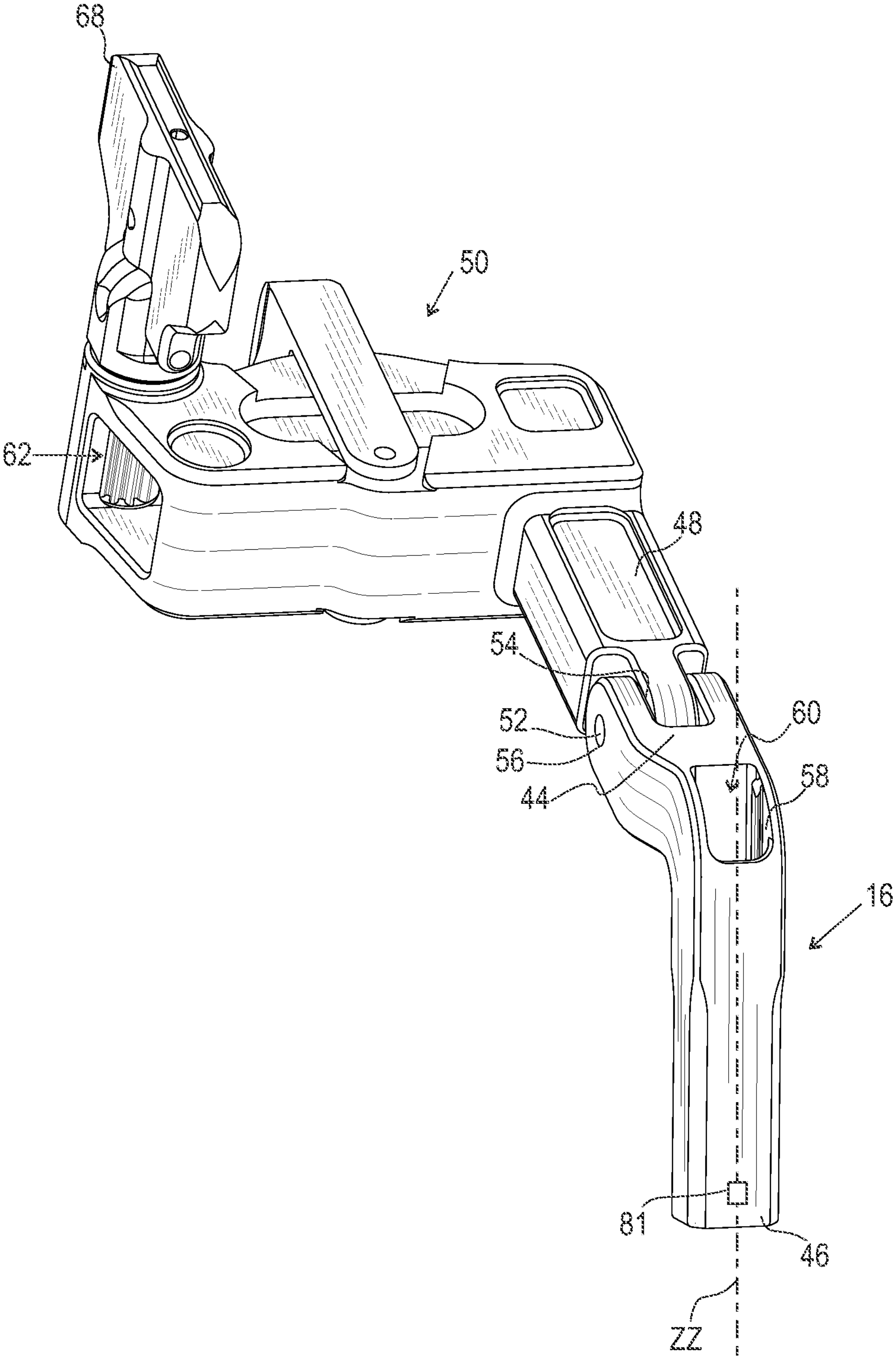
FIG. 3 is a perspective view of components of the surgical system shown in FIG. 1.
Figure 4:
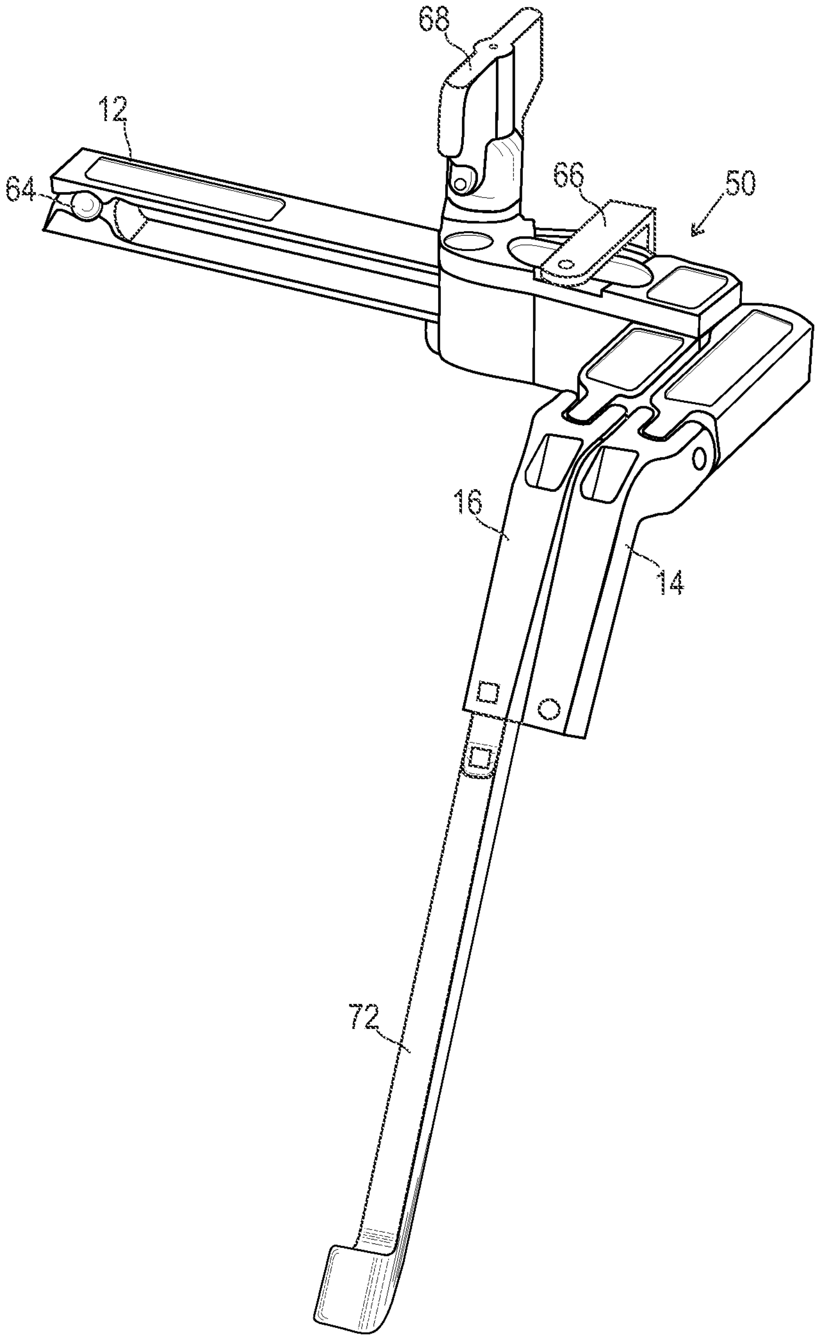
FIG. 4 is a perspective view of components of the surgical system of FIG. 1.
Figure 5:
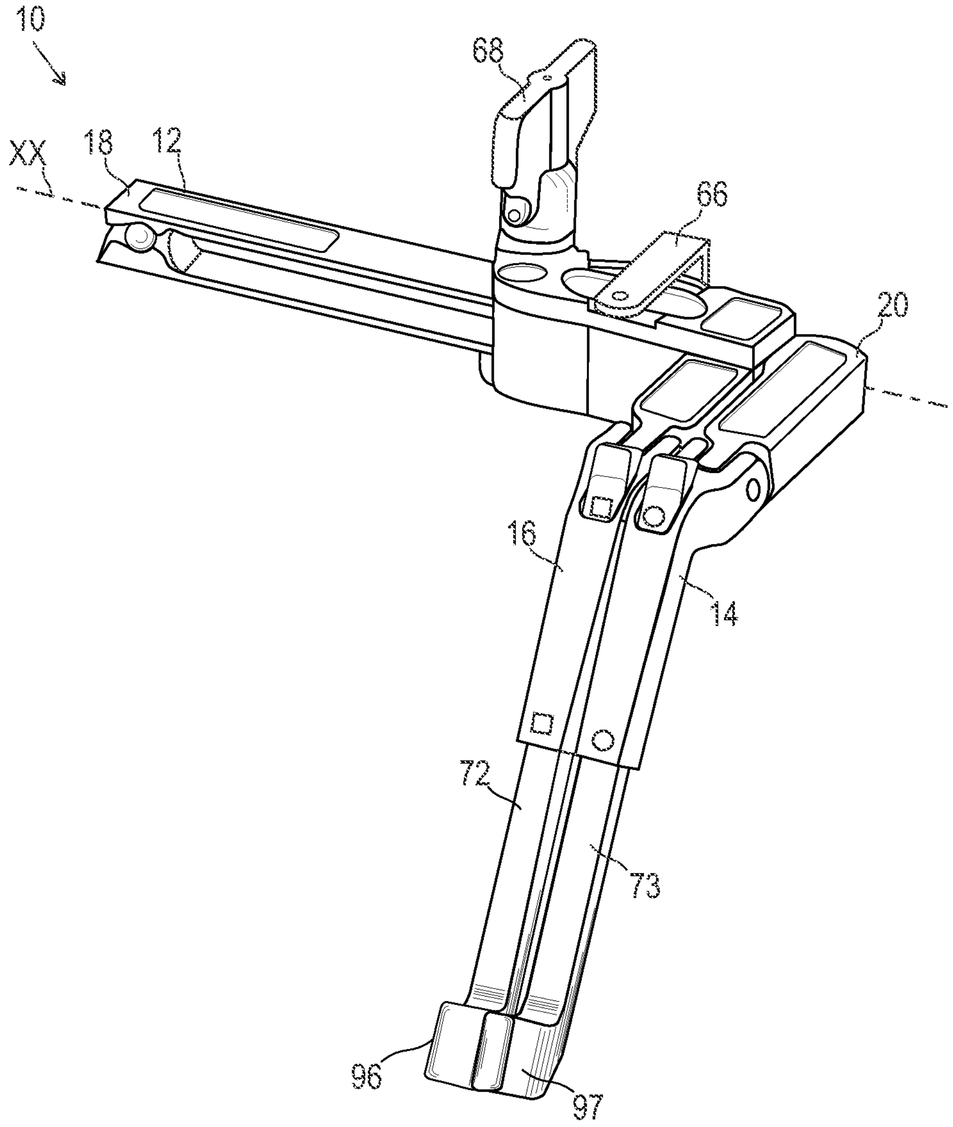
FIG. 5 is a perspective view of the components of the surgical system of FIG. 1.

Rack 12 extends between an end 18 and an end 20 and defines a longitudinal axis XX, as shown in FIG. 5. Rack 12 includes a ratchet configuration including an outer surface 22 that defines a plurality of teeth, for example, splines 24 engageable with a portion of arm 16 such that arm 16 is translatable relative to longitudinal axis XX in a bi-directional and/or two-way ratchet configuration, as shown in FIGS. 2-4 and described herein.

Figure 2:
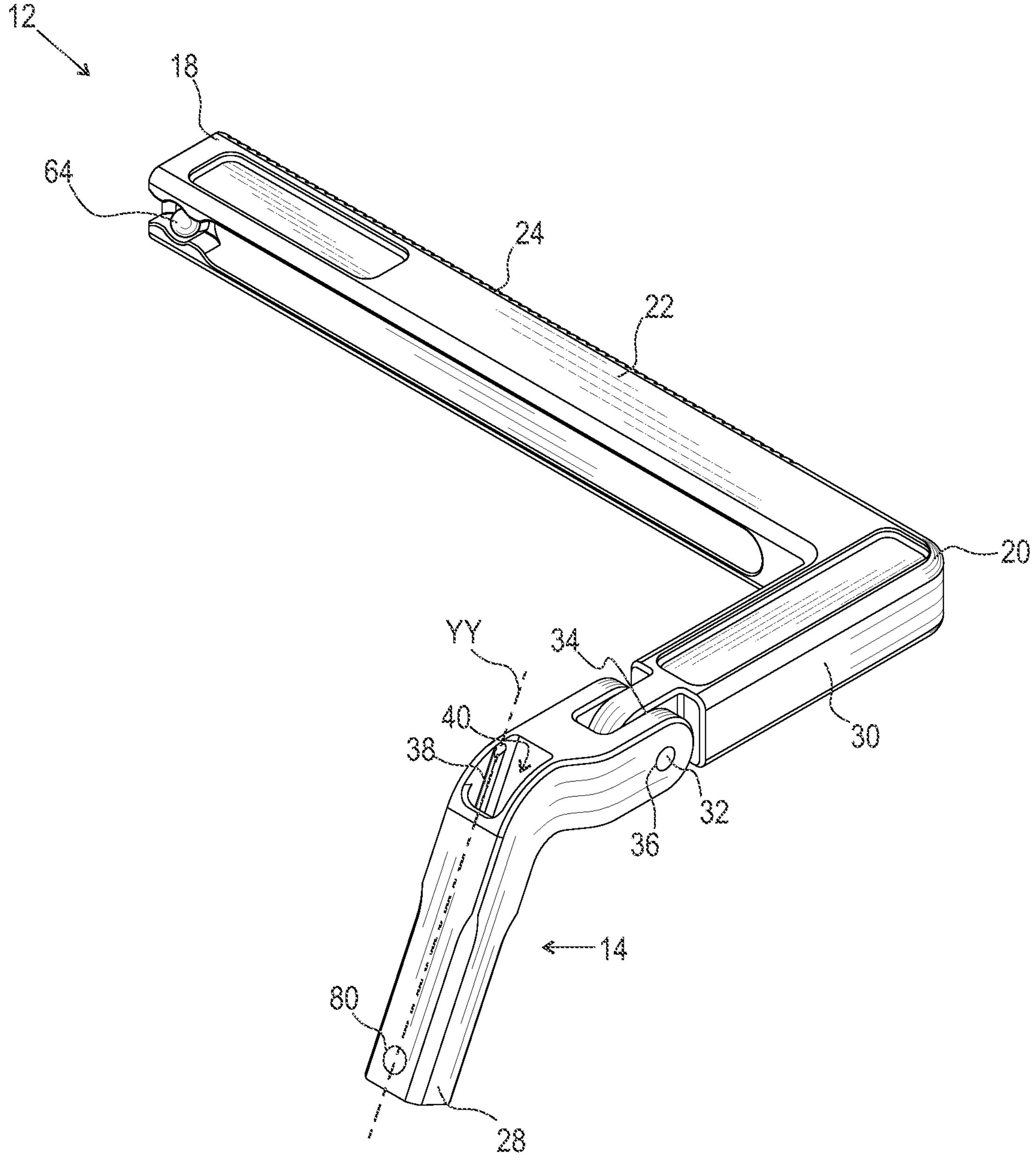
FIG. 2 is a perspective view of components of the surgical system shown in FIG. 1.

End 20 is configured for connection with arm 14, as shown in FIG. 2. Arm 14 extends between an end 26 and an end 28 and defines a longitudinal axis YY. Longitudinal axis YY is transverse relative to longitudinal axis XX. In some embodiments, arm 14 is solid. In some embodiments, all or a portion of arm 14 is solid. In some embodiments, arm 14 may have alternately shaped configurations, for example, oval, oblong, triangular, square, polygonal, irregular, uniform, non-uniform, offset, staggered, undulating, arcuate, variable and/or tapered. In some embodiments, arm 14 may have alternate surface configurations, for example, smooth, rough, arcuate, undulating, porous, semi-porous, dimpled, polished and/or textured.

End 26 engages with an extension 30 of end 20 via disposal of a pin 32 through an opening 34 of extension 30 and an opening 36 of end 26. In some embodiments, arm 14 is engageable with extension 30, for example, via clips, hooks, adhesives and/or flanges.

Figure 11:
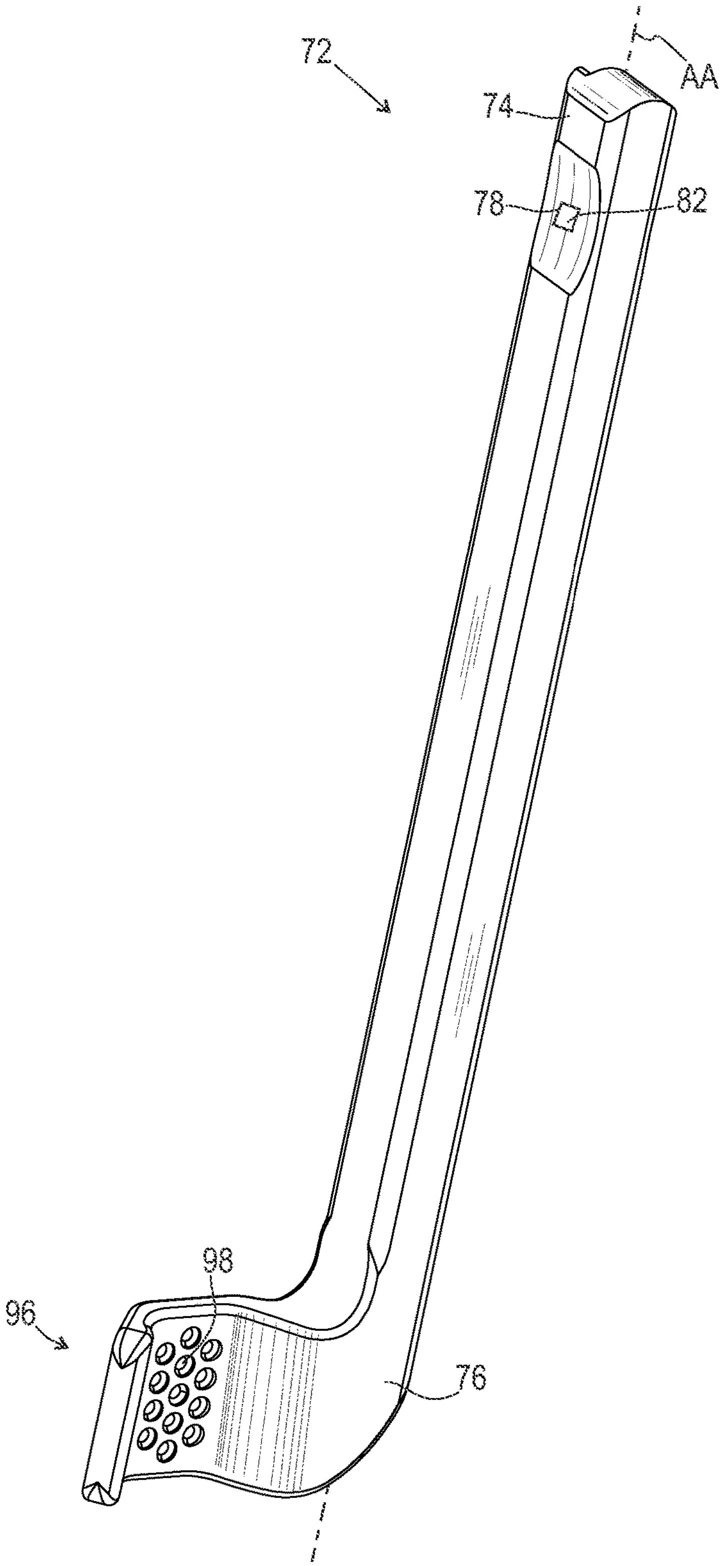
FIG. 11 is a perspective view of components of one embodiment of a surgical system in accordance with the principles of the present disclosure.
Figure 12:
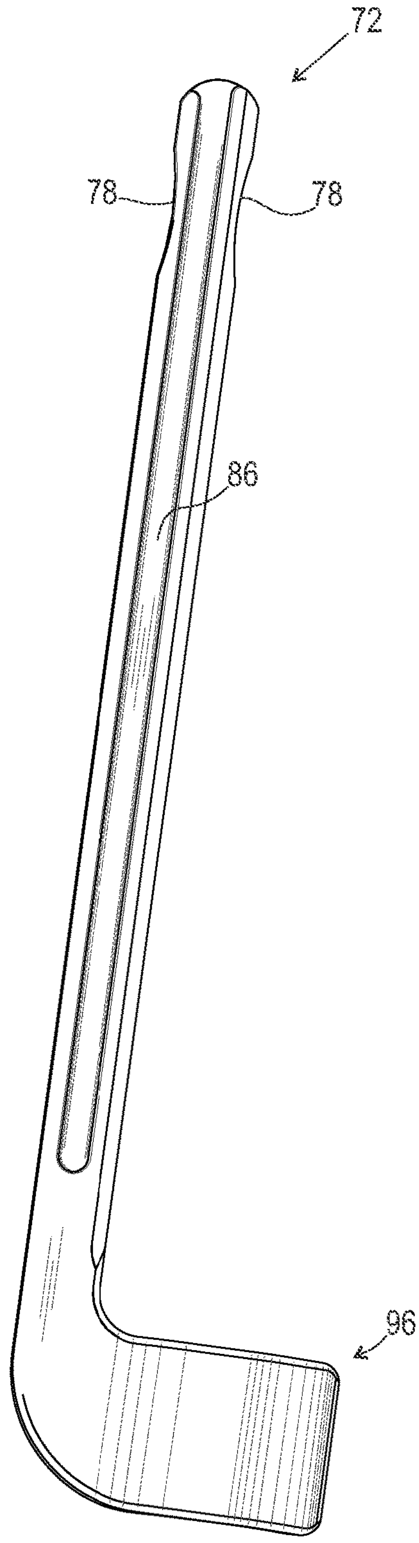
FIG. 12 is a perspective view of the components shown in FIG. 11.

Arm 14 includes an inner surface 38 that defines a passageway 40, as shown in FIG. 2. Passageway 40 is configured to receive the engaging surfaces, as shown in FIGS. 11-12 and described herein. The engaging surfaces are configured for engagement with vertebral tissue and are selected according to the particular vertebral tissue that is being distracted and/or compressed. In some embodiments, passageway 40 may have alternate surface configurations, for example, smooth, rough, arcuate, undulating, porous, semi-porous, dimpled, polished and/or textured.

Arm 16 extends between an end 44 and an end 46 and defines a longitudinal axis ZZ, as shown in FIG. 3. Longitudinal axis ZZ is parallel to longitudinal axis YY and is transverse relative to longitudinal axis XX. In some embodiments, arm 16 is solid. In some embodiments, all or a portion of arm 16 is solid. In some embodiments, arm 16 may have alternately shaped configurations, for example, oval, oblong, triangular, square, polygonal, irregular, uniform, non-uniform, offset, staggered, undulating, arcuate, variable and/or tapered. In some embodiments, arm 16 may have alternate surface configurations, for example, smooth, rough, arcuate, undulating, porous, semi-porous, dimpled, polished and/or textured.

End 44 engages with an extension 48 engaged to a mount 50 via disposal of a pin 52 through an opening 54 of extension 48 and an opening 56 of end 44. In some embodiments, arm 16 is engageable with extension 48, for example, via clips, hooks, adhesives and/or flanges.

Arm 16 includes an inner surface 58 that defines a passageway 60, as shown in FIG. 3. Passageway 60 is configured to receive the engaging surfaces, as shown in FIGS. 11-12 and described herein. In some embodiments, passageway 60 may have alternate surface configurations, for example, smooth, rough, arcuate, undulating, porous, semi-porous, dimpled, polished and/or textured.

Mount 50 includes a surface that defines an opening 62 configured for disposal of surface 22 of rack 12 for mounting arm 16 with rack 12, as shown in FIGS. 2-4. Mount 50 is configured to facilitate translation of arm 16 relative to rack 12. In some embodiments, arm 16 is engageable with rack 12, for example, via clips, hooks, adhesives and/or flanges. End 18 of rack 12 includes a ball 64 that is spring loaded, as shown in FIGS. 2 and 4. Mount 50 is configured to contact ball 64 when mount 50 is translated in the direction of end 18 and prevents mount 50 from disengaging from rack 12 during translation.

Rack 12 includes a ratchet configuration, including splines 24 and opening 62 of mount 50 engageable in a bi-directional and/or two-way ratchet configuration. Mount 50 includes a latch 66 that includes a pinion or pawl (not shown) engageable with splines 24. Latch 66 is pivotable relative to mount 50 for disposal in a distraction position, as described herein. In the distraction position, latch 66 engages rack 12 to allow axial and/or incremental translation of arm 16 relative to arm 14/rack 12 and prevents axial translation of arm 16 relative to arm 14/rack 12, in an opposing direction. As such, distraction of vertebral tissue connected with the engaging surfaces can be performed.

Latch 66 is pivotable relative to mount 50. For example, latch 66 is pivotable for disposal in a neutral position. In the neutral position, latch 66 disengages from rack 12 to allow free axial translation of arm 16 relative to arm 14/rack 12. Latch 66 is pivotable relative to mount 50 for disposal in a compression position (not shown). In the compression position, latch 66 engages rack 12 to allow axial and/or incremental translation of arm 16 relative to arm 14/rack 12 to compress vertebral tissue and prevents axial translation of arm 16 relative to arm 14/rack 12, in an opposing direction. As such, compression of vertebral tissue connected with the engaging surfaces can be performed. In some embodiments, a rotatable key 68 includes a gear surface (not shown) engageable with splines 24 to axially and/or incrementally translate rack 12 to facilitate distraction and/or compression, as described herein.

Figure 10:
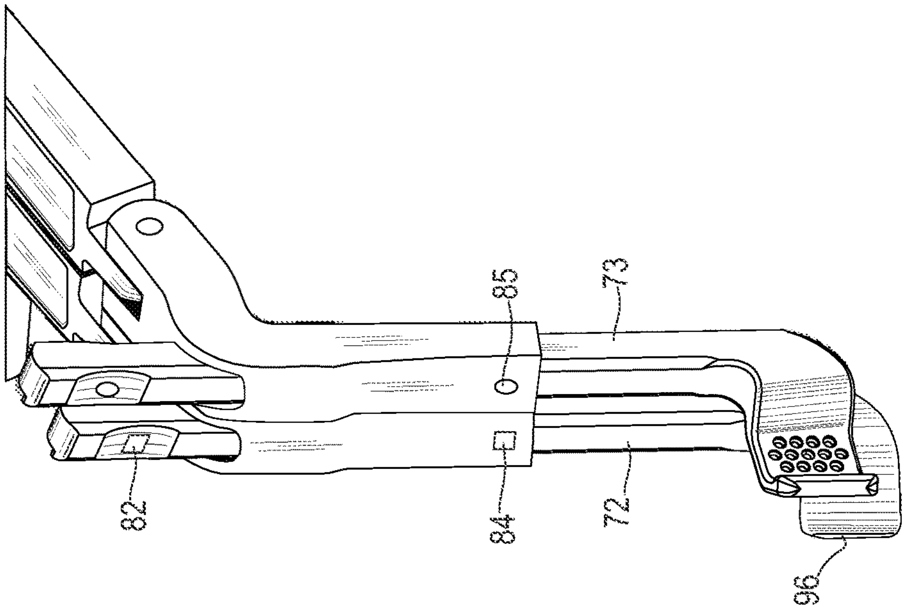
FIG. 10 is a break away view of components of the surgical system shown in FIG. 1.
Figure 13:
FIG. 13 is a perspective view of components of one embodiment of a surgical system in accordance with the principles of the present disclosure disposed with vertebrae.
Figure 14:
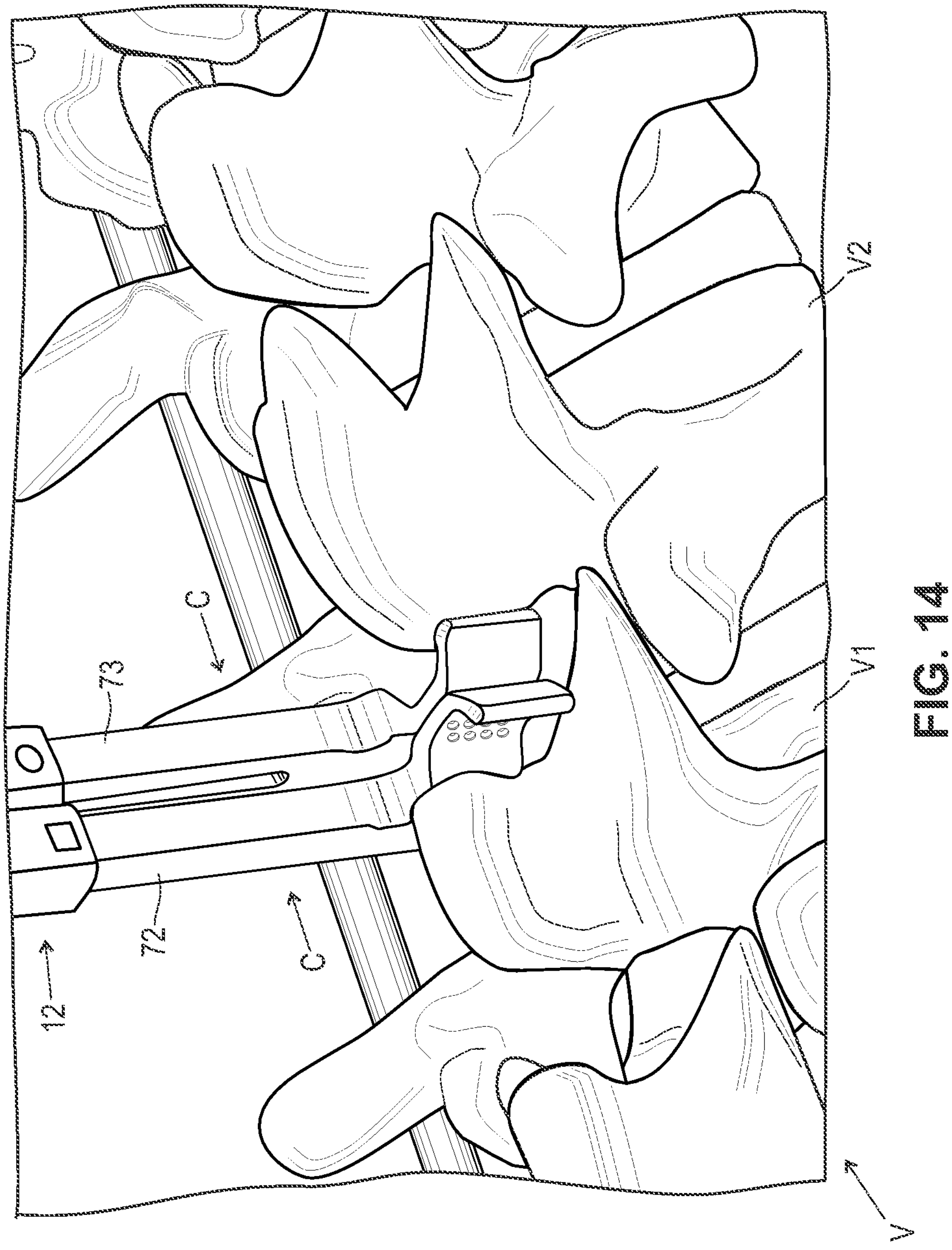
FIG. 14 is a break away view of components of the surgical system and vertebrae shown in FIG. 13.

The engaging surfaces include leg 72 and leg 73, similar to leg 72, as shown in FIGS. 1 and 11-12. Legs 72, 73 are connectable with arms 14, 16 and are selected for engagement with spinous process tissue, as shown in FIGS. 13 and 14. Leg 72 includes an end 74, an end 76 and a longitudinal axis AA disposed therebetween. End 74 includes a mating surface 78 configured for connection with a mating surface 80 of arm 14 or a mating surface 81 of arm 16. Mating surface 78 includes a projection 82 and mating surfaces 80 and 81 define openings 84, 85 that are configured to receive projection 82, as shown in FIG. 10. Projection 82 and openings 84, 85 are configured to facilitate accurate assembly of arms 14, 16 with leg 72. Projection 82 includes a square or circular shape that corresponds with a square or circular shape openings 84, 85 as shown in FIG. 10. In some embodiments, projection 82 and openings 84, 85 are variously shaped and include rectangular, star, triangular, hexagonal, octagonal, uniform and/or irregular configurations. In some embodiments, projection 82 and openings 84, 85 alternatively include adhesive labels that matingly correspond to each other. In some embodiments, the adhesive labels are variously configured and include a circular, square, rectangular, star, triangular, hexagonal, octagonal, uniform and/or irregular shaped configurations.

Figure 9:
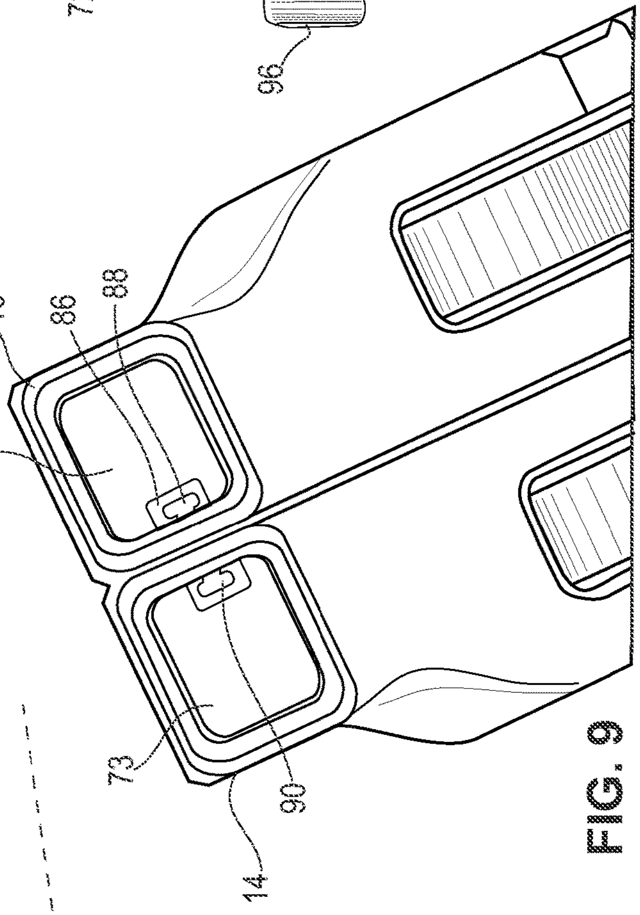
FIG. 9 is a break away view of components of the surgical system shown in FIG. 1.
Figure 8:
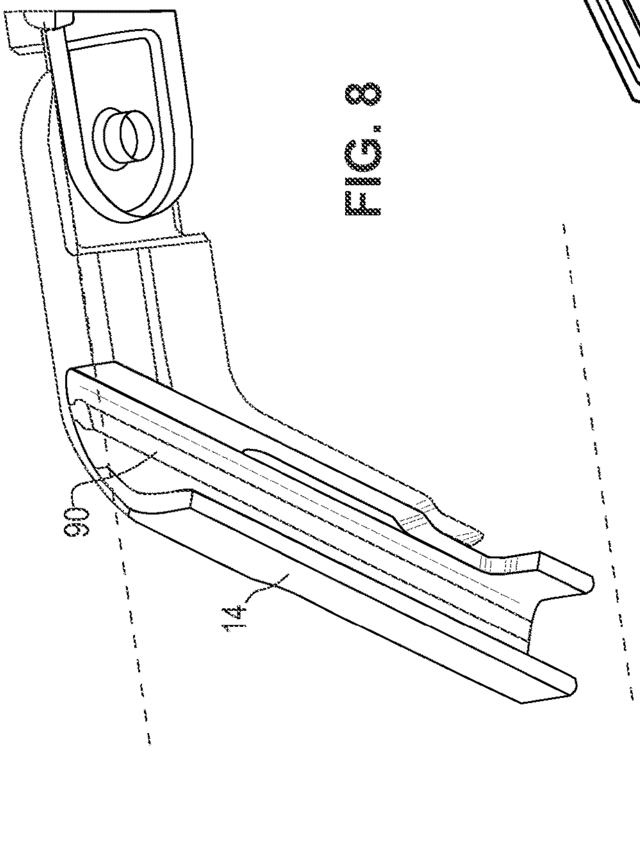
FIG. 8 is a cross-section view of components of the surgical system shown in FIG. 1.

An exterior surface of leg 72 defines a longitudinal groove 86 configured for slidable engagement with an interior rail 88 of arm 16 and/or an interior rail 90 of arm 14 to form a dovetail connection, as shown in FIGS. 8, 9 and 12. In some embodiments, longitudinal groove 86 may be variously oriented relative to axis AA, for example, parallel, perpendicular, angular and/or offset. In some embodiments, longitudinal groove 86 may have alternate surface configurations, for example, smooth, rough, arcuate, undulating, porous, semi-porous, dimpled, polished and/or textured. In some embodiments, interior rails 88, 90 may be variously oriented relative to axis YY and/or ZZ, for example, parallel, perpendicular, angular and/or offset. In some embodiments, interior rails 88, 90 may have alternate surface configurations, for example, smooth, rough, arcuate, undulating, porous, semi-porous, dimpled, polished and/or textured.

Figure 7:
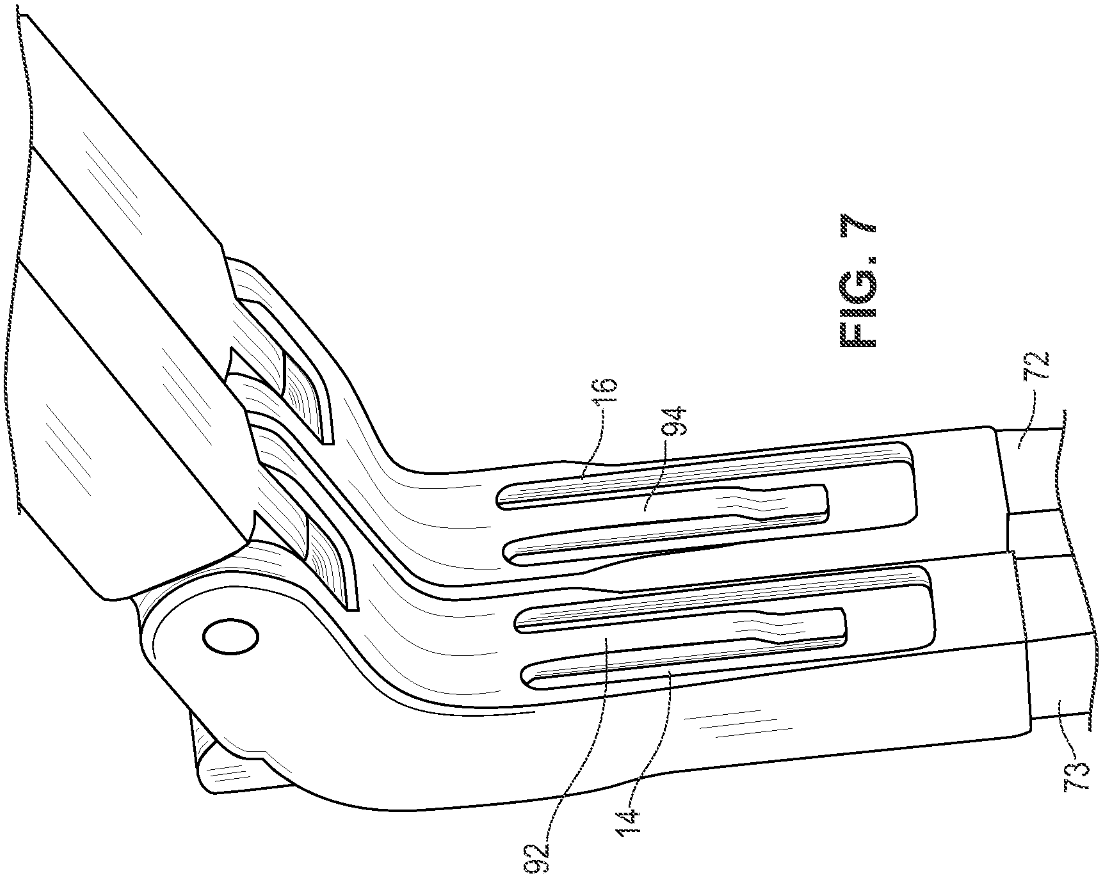
FIG. 7 is a break away view of components of the surgical system shown in FIG. 1.
Figure 6:
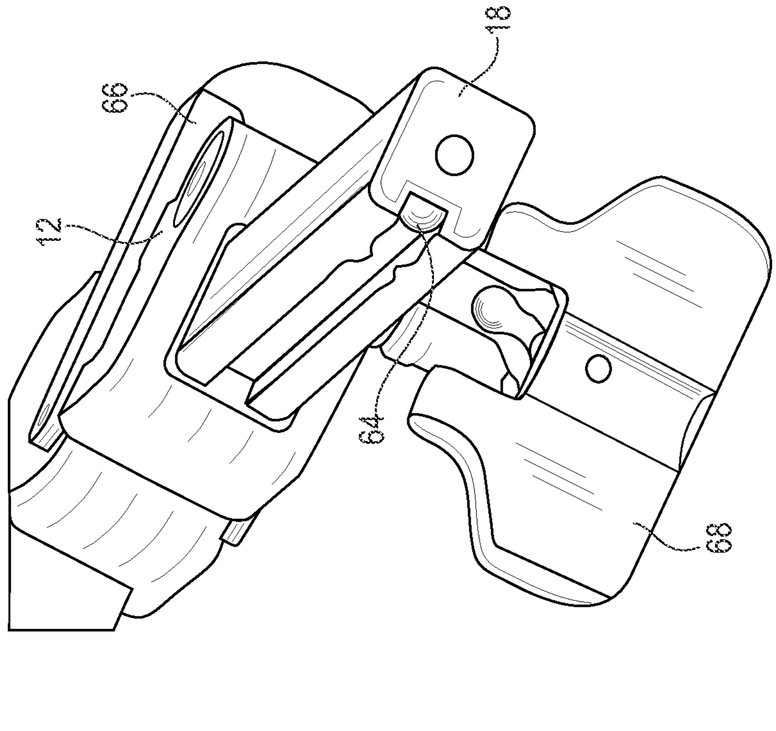
FIG. 6 is a break away view of components of the surgical system shown in FIG. 1.

Arm 14 includes a longitudinal tab 92 and arm 16 includes a longitudinal tab 94, as shown in FIG. 7. Leg 72 is connectable with arms 14 and/or 16 via a friction fit connection formed between an exterior surface of arms 14, 16 and longitudinal tabs 92 and/or 94. In some embodiments, the friction connection enables height adjustment of leg 72. In some embodiments, longitudinal tabs 92 and/or 94 may be variously oriented relative to axis YY and/or ZZ, for example, parallel, perpendicular, angular and/or offset. In some embodiments, longitudinal tabs 92 and/or 94 may have alternate surface configurations, for example, smooth, rough, arcuate, undulating, porous, semi-porous, dimpled, polished and/or textured.

End 76 includes a capturing element 96, as shown in FIGS. 11 and 12, configured for engagement with spinous process tissue. Capturing element 96 includes a bracket configuration for engagement with the spinous process tissue. Capturing element 96 includes a textured gripping surface 98 configured to facilitate gripping of surfaces of the spinous process tissue during distraction of the spinous process tissue. In some embodiments, textured gripping surface 98 may have alternate surface configurations, for example, smooth, rough, arcuate, undulating, porous, semi-porous, dimpled, polished and/or textured.

In assembly, operation and use, surgical system 10, similar to the systems and methods described herein, is employed with a surgical procedure, for treatment of a spine of a patient including vertebrae V, as shown in FIGS. 13-14. Surgical system 10 may also be employed with surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

Surgical system 10 is employed with a procedure for treatment of an applicable condition or injury of an affected section of a spinal column and adjacent areas within a body. For example, vertebrae V includes a vertebral level V1 and a vertebral level V2, as shown in FIG. 13. In some embodiments, components of surgical system 10 are configured for insertion with a vertebral space to space apart vertebral tissue, provide support and maximize stabilization of vertebrae V.

In use, to treat an affected section of vertebrae V, a medical practitioner obtains access to a surgical site including vertebrae V in any appropriate manner, such as through incision and retraction of tissues. In some embodiments, surgical system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area.

An incision is made in the body of a patient and a cutting instrument (not shown) creates a surgical pathway for implantation of components of surgical system 10. A preparation instrument (not shown) can be employed to prepare tissue surfaces of vertebrae V, as well as for aspiration and irrigation of a surgical region.

Rack 12 via arms 14, 16 is connected with a pair of engaging surfaces, for example, legs 72, 73, as shown in FIG. 13, to allow for distraction and/or compression of vertebrae V, at for example, the spinous process. A capturing element 96 of leg 72 and a capturing element 97 of leg 73 engage with the vertebral tissue, for example, surfaces of the spinous process. Latch 66 is rotated relative to mount 50 in a direction, as shown by arrow A in FIG. 13, to dispose rack 12 in a distraction position, as described herein. In the distraction position, latch 66 engages rack 12 to allow axial and/or incremental translation of arm 16 relative to arm 14/rack 12 and prevents axial translation of arm 16 relative to arm 14/rack 12, in an opposing direction. As such, distraction of vertebral tissue can be performed.

Latch 66 is pivotable relative to mount 50 for example, for disposal in a neutral position. In the neutral position, latch 66 disengages from rack 12 to allow free axial translation of arm 16 relative to arm 14/rack 12. Rotatable key 68 is engageable with splines 24 to axially and/or incrementally translate rack 12 to facilitate distraction and/or compression, as described herein. For example, latch 66 is pivotable to the distraction position to allow translation of arm 16, in a direction shown by arrows B in FIG. 13, while arm 14 is fixed. Distraction of vertebrae V1, V2 can be performed. To adjust the distance of distraction, arm 16 is axially translated in a direction shown by arrows C in FIG. 14. In some embodiments, to compress a selected section of vertebrae, arm 16 is axially translated in the direction shown by arrows C in FIG. 14. In some embodiments, rack 12 is connected with a selected engaging surface to allow for engagement, distraction and/or compression of vertebrae V, at for example, the laminae process and/or attachment to bone fasteners, including pedicle screws.

In some embodiments, a light source is disposed with rack 12 to provide illumination to the working channel. In some embodiments, rack 12 is employed in segmental distraction to facilitate insertion of an interbody implant and for decompressing tissue.

Upon completion of a procedure, as described herein, the surgical instruments, assemblies and non-implanted components of surgical system 10 are removed and the incision(s) are closed. One or more of the components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10. In some embodiments, surgical system 10 may include one or a plurality of plates, connectors and/or bone fasteners for use with a single vertebral level or a plurality of vertebral levels.

In some embodiments, surgical system 10 includes one or a plurality of alternate surgical instruments, each configured for mating engagement in a quick release configuration with spinal constructs, rack 12 and/or other surgical instruments, as described herein. This configuration facilitates the interchangeability of the spinal constructs with the alternate surgical instruments. In some embodiments, surgical system 10 includes one or a plurality of alternate surgical instruments, such as, for example, inserters, extenders, reducers, spreaders, distractors, blades, retractors, clamps, forceps, elevators and drills, which may be alternately sized and dimensioned, and arranged as a kit.

In some embodiments, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration.

Figure 15:
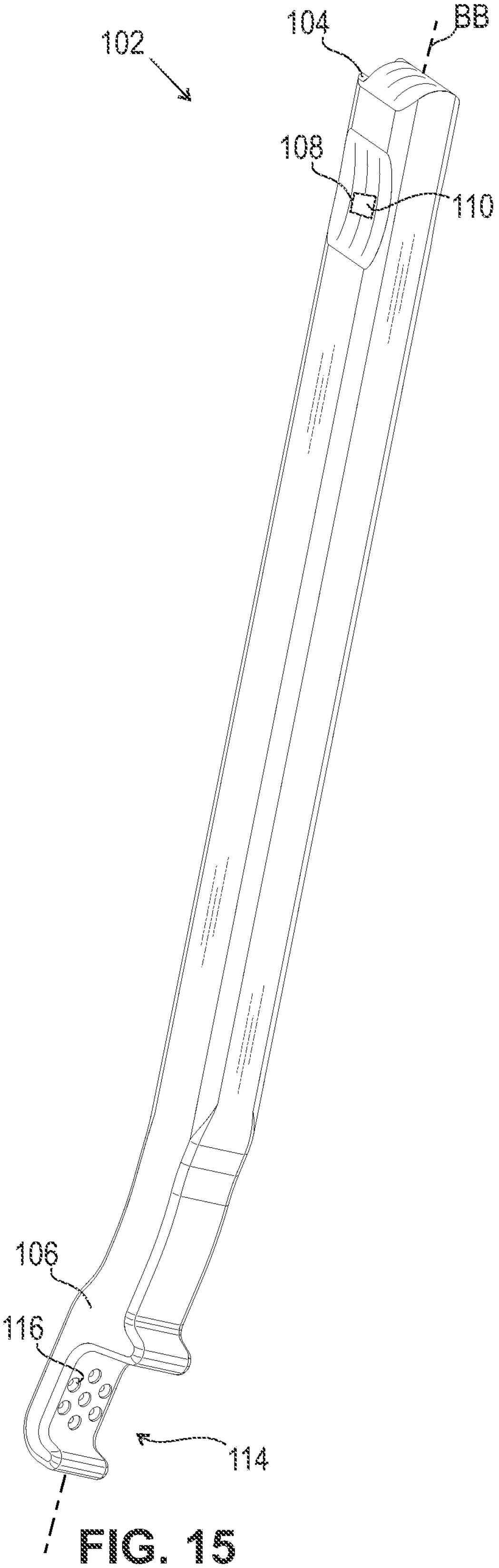
FIG. 15 is a perspective view of components of one embodiment of a surgical system in accordance with the principles of the present disclosure.
Figure 16:
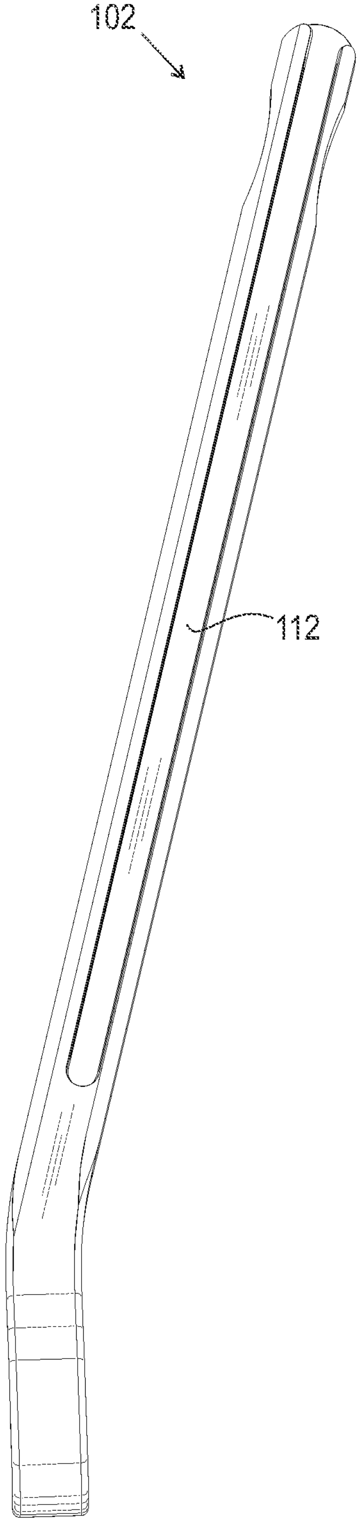
FIG. 16 is a perspective view of the components shown in FIG. 15.

In one embodiment, as shown in FIGS. 15-16, surgical system 10, similar to the systems and methods described with regard to FIGS. 1-14, includes engaging surfaces, for example, a leg 102, similar to leg 72. Leg 102 is connectable and/or interchangeable with arms 14, 16, as described herein, and configured to engage laminae tissue. Leg 102 includes an end 104, an end 106 and a longitudinal axis BB disposed therebetween. End 104 includes a mating surface 108, similar to mating surface 78 described herein, configured for connection with mating surfaces 80, 81 of arms 14, 16. Mating surface 108 includes a projection 110, similar to projection 82 described herein with regard to FIGS. 11-12, that is configured to be received by openings 84, 85 of mating surfaces 80, 81.

An exterior surface of leg 102 defines a longitudinal groove 112, similar to longitudinal groove 86 described herein with regard to FIGS. 11-12, configured for slidable engagement with interior rail 90 of arm 14 and/or interior rail 88 of arm 16 to form a dovetail connection. In some embodiments, longitudinal groove 112 may be variously oriented relative to axis BB, for example, parallel, perpendicular, angular and/or offset.

End 106 includes a capturing element 114, similar to capturing element 96, as shown in FIGS. 11-12. Capturing element 114 is configured for engagement with laminae tissue. Capturing element 114 includes a C-shaped configuration for engagement with the laminae tissue. Capturing element 114 includes a textured gripping surface 116, similar to textured gripping surface 98 described herein with regard to FIGS. 11-12, configured to facilitate gripping of surfaces of the laminae tissue during distraction of the vertebral tissue. In some embodiments, textured gripping surface 116 may have alternate surface configurations, for example, smooth, rough, arcuate, undulating, porous, semi-porous, dimpled, polished and/or textured.

Rack 12 via arms 14, 16 is connected with leg 102 to allow for distraction and/or compression of vertebrae V, at for example, the laminae. Capturing element 114 engages with the laminae tissue, for example, surfaces of the laminae during distraction and/or compression.

Figure 17:
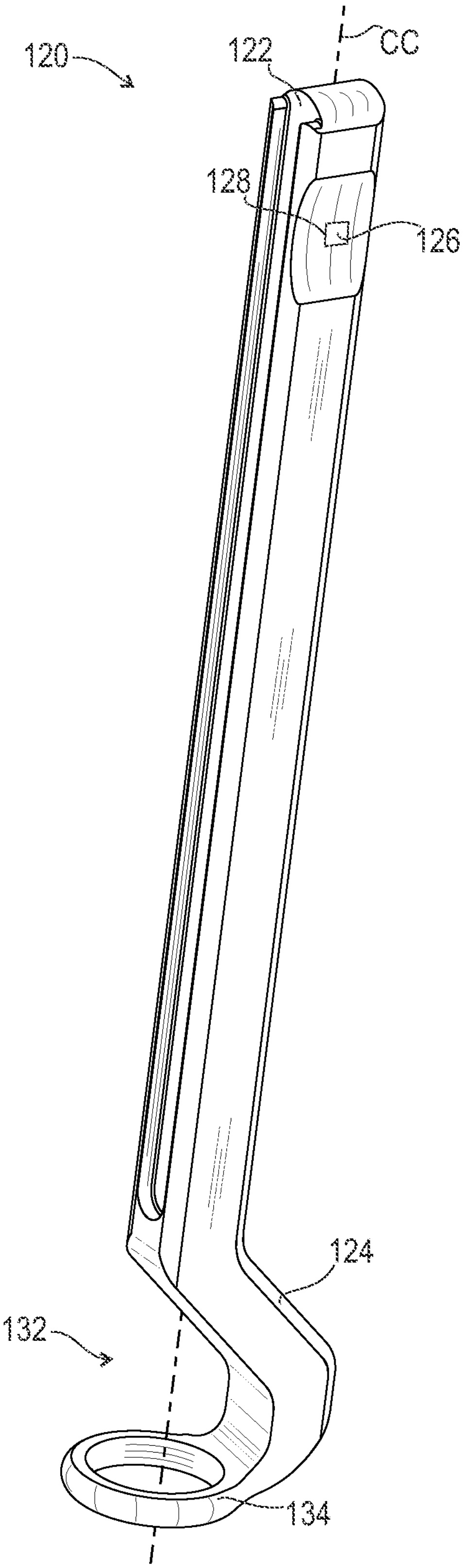
FIG. 17 is a perspective view of components of one embodiment of a surgical system in accordance with the principles of the present disclosure.
Figure 18:
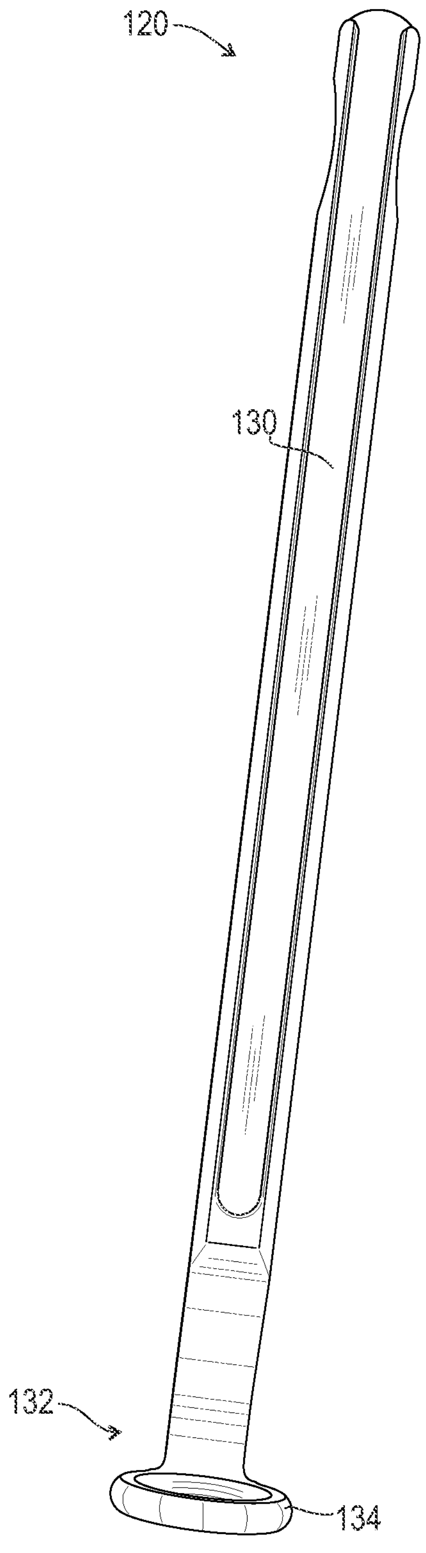
FIG. 18 is a perspective view of the components shown in FIG. 17.

In one embodiment, as shown in FIGS. 17-18, surgical system 10, similar to the systems and methods described herein with regard to FIGS. 1-14, includes engaging surfaces, for example, a leg 120, similar to leg 72. Leg 120 is connectable and/or interchangeable with arms 14, 16, as described herein, and configured to engage with a spinal implant, for example, a bone fastener (not shown) that is connected to vertebral tissue. Leg 120 includes an end 122, an end 124 and a longitudinal axis CC disposed therebetween. End 122 includes a mating surface 126, similar to mating surface 78, described herein with regard to FIGS. 11 and 12, configured for connection with mating surfaces 80, 81 of arms 14, 16. Mating surface 126 includes a projection 128, similar to projection 82 described herein with regard to FIGS. 11-12, that is configured to be received by openings 84, 85 of mating surfaces 80, 81.

An exterior surface of leg 120 defines a longitudinal groove 130, similar to longitudinal groove 86 described herein with regard to FIGS. 11-12, configured for slidable engagement with interior rail 90 of arm 14 and/or interior rail 88 of arm 16 to form a dovetail connection. In some embodiments, longitudinal groove 130 may be variously oriented relative to axis CC, for example, parallel, perpendicular, angular and/or offset.

End 124 is angled and includes a capturing element 132, similar to capturing element 96, as shown in FIGS. 11-12. Capturing element 132 is configured for engagement with a bone fastener fixed with vertebral tissue. Capturing element 132 includes a ring 134 for engagement with the bone fastener fixed with the vertebral tissue.

Rack 12 via arms 14, 16 is connected with leg 120 to allow for distraction and/or compression of vertebrae V that is fixed with one or more bone fasteners. Capturing element 132 engages with a bone fastener during distraction and/or compression.

Figure 19:
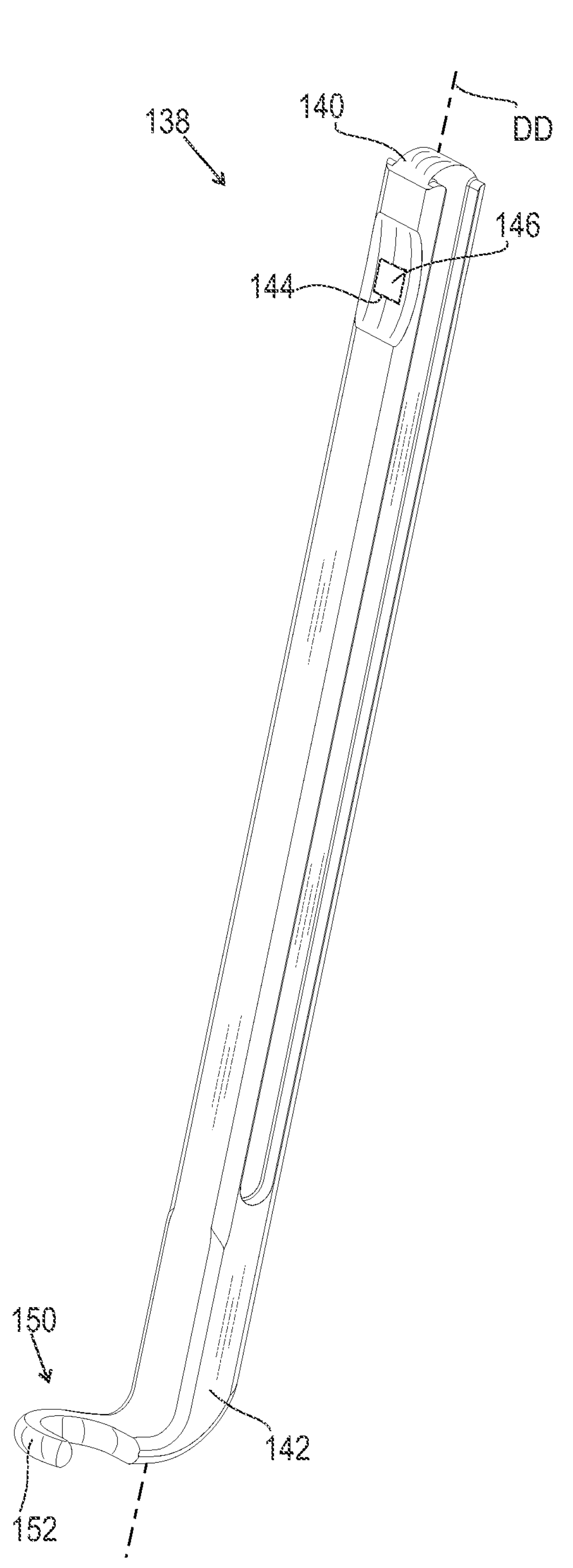
FIG. 19 is a perspective view of components of one embodiment of a surgical system in accordance with the principles of the present disclosure.
Figure 20:
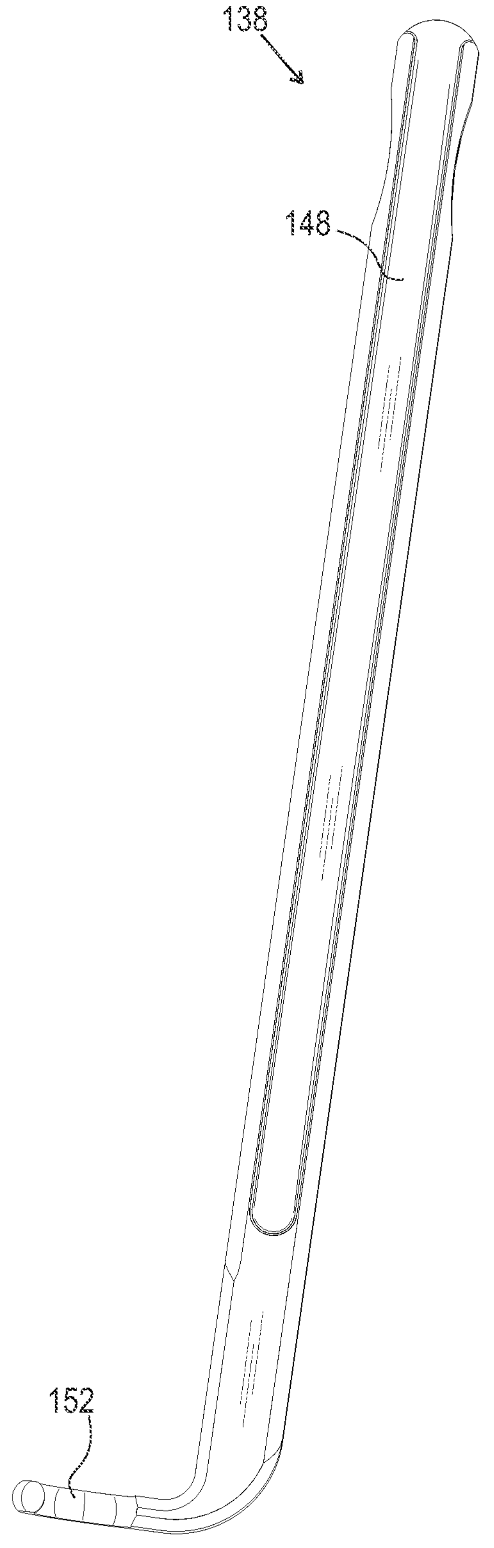
FIG. 20 is a perspective view of the components shown in FIG. 19.

In one embodiment, as shown in FIGS. 19-20, surgical system 10, similar to the systems and methods described herein with regard to FIGS. 1-14, includes engaging surfaces, for example, a leg 138, similar to leg 72. Leg 138 is connectable and/or interchangeable with arms 14, 16, as described herein, and configured to engage with a spinal implant, for example, a bone fastener (not shown) that is connected to vertebral tissue. Leg 138 includes an end 140, an end 142 and a longitudinal axis DD disposed therebetween. End 140 includes a mating surface 144, similar to mating surface 78, described herein with regard to FIGS. 11 and 12, configured for connection with mating surfaces 80, 81 of arms 14, 16. Mating surface 144 includes a projection 146, similar to projection 82 described herein with regard to FIGS. 11-12, that is configured to be received by openings 84, 85 of mating surfaces 80, 81.

An exterior surface of leg 138 defines a longitudinal groove 148, similar to longitudinal groove 86 described herein with regard to FIGS. 11-12, configured for slidable engagement with interior rail 90 of arm 14 and/or interior rail 88 of arm 16 to form a dovetail connection. In some embodiments, longitudinal groove 148 may be variously oriented relative to axis DD, for example, parallel, perpendicular, angular and/or offset.

End 142 includes a capturing element 150, similar to capturing element 96, as shown in FIGS. 11-12. Capturing element 150 is configured for engagement with a bone fastener fixed with vertebral tissue. Capturing element 150 includes a hook 152 for engagement with the bone fastener fixed with the vertebral tissue.

Rack 12 via arms 14, 16 is connected with leg 138 to allow for distraction and/or compression of vertebrae V that is fixed with one or more bone fasteners. Capturing element 150 engages with a bone fastener during distraction and/or compression.

Figure 21:
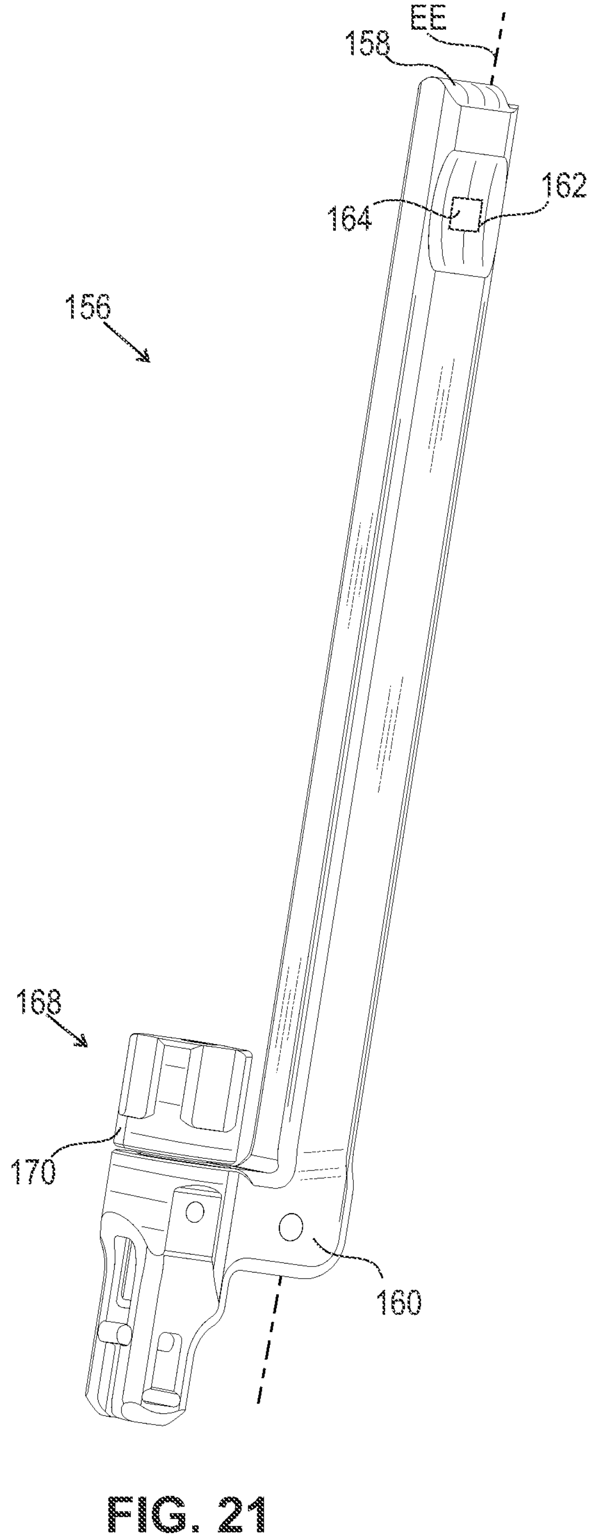
FIG. 21 is a perspective view of components of one embodiment of a surgical system in accordance with the principles of the present disclosure.
Figure 22:
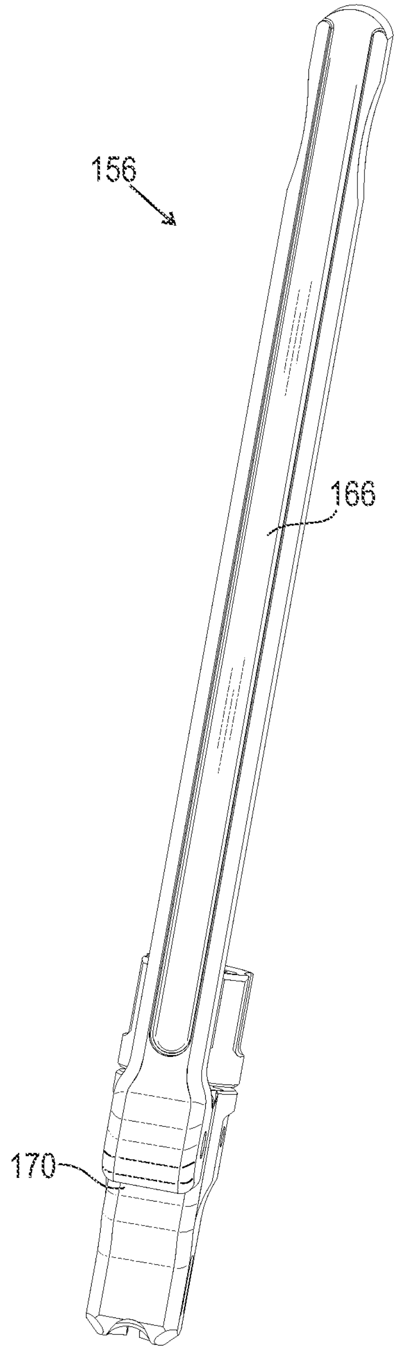
FIG. 22 is a perspective view of the components shown in FIG. 21.

In one embodiment, as shown in FIGS. 21-22, surgical system 10, similar to the systems and methods described herein with regard to FIGS. 1-14, includes engaging surfaces, for example, a leg 156 similar to leg 72. Leg 156 is connectable and/or interchangeable with arms 14, 16, as described herein, and configured to engage with a spinal implant, for example, a bone fastener (not shown) that is connected to vertebral tissue. Leg 156 includes an end 158, an end 160 and a longitudinal axis EE disposed therebetween. End 158 includes a mating surface 162, similar to mating surface 78, described herein with regard to FIGS. 11-12, configured for connection with mating surfaces 80, 81 of arms 14, 16. Mating surface 162 includes a projection 164, similar to projection 82 described herein with regard to FIGS. 11-12, that is configured to be received by openings 84, 85 of mating surfaces 80, 81.

An exterior surface of leg 156 defines a longitudinal groove 166, similar to longitudinal groove 86 described herein with regard to FIGS. 11-12, configured for slidable engagement with interior rail 90 of arm 14 and/or interior rail 88 of arm 16 to form a dovetail connection. In some embodiments, longitudinal groove 166 may be variously oriented relative to axis EE, for example, parallel, perpendicular, angular and/or offset.

End 160 includes a capturing element 168, similar to capturing element 96, as shown in FIGS. 11-12. Capturing element 168 is configured for engagement with a bone fastener fixed with vertebral tissue. Capturing element 168 includes a connector 170 configured for engagement with the bone fastener fixed with the vertebral tissue.

Rack 12 via arms 14, 16 is connected with leg 156 to allow for distraction and/or compression of vertebrae V that is fixed with one or more bone fasteners. Capturing element 168 engages with a bone fastener during distraction and/or compression.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical system comprising:

non-cannulated first and second legs;

a first member defining a first passageway extending along a first axis, the first leg being disposed within the first passageway such that a proximal end of the first leg extends through a proximal opening of the first passageway, a first projection of the first leg extends through a first opening of the first member, and a distal end of the first leg extends through a distal opening of the first passageway, the first projection extending transverse to the first axis;

a second member defining a second passageway extending along a second axis, the second leg being disposed within the second passageway such that a proximal end of the second leg extends through a proximal opening of the second passageway, a second projection of the second leg extends through a second opening of the second member, and a distal end of the first leg extends through a distal opening of the second passageway, the second projection extending transverse to the second axis, the members being relatively movable between a first orientation in which the first member directly engages the second member and a second orientation in which the members are spaced apart from one another to distract and/or compress vertebral tissue, and the legs each being configured for slidable engagement with the members to form a dovetail connection and prevent rotation of the legs relative to the members.

2. A surgical system as recited in claim 1, further comprising a toothed rack engageable with the first member and the second member.

3. A surgical system as recited in claim 1, wherein the first member includes a tubular arm configured to receive the first leg such that an inner surface of the first member that defines the first passageway engages an outer surface of the first leg.

4. A surgical system as recited in claim 1, wherein:

the first member includes a tubular arm configured for disposal of the first leg such that an inner surface of the first member that defines the first passageway engages an outer surface of the first leg; and the second member includes a tubular arm configured for disposal of the second leg such that an inner surface of the second member that defines the second passageway engages an outer surface of the second leg.

5. A surgical system as recited in claim 1, wherein the first leg includes a mating surface configured for connection with the first member and the second leg includes a mating surface configured for connection with the second member.

6. A surgical system as recited in claim 5, wherein the mating of the first leg includes an outer surface of the first leg that is engageable with an inner surface of the first member that defines the first passageway.

7. A surgical system as recited in claim 1, wherein the first opening and the first projection are square and the second opening and the second projection are circular.

8. A surgical system as recited in claim 1, wherein the first member extends 360 degrees about a portion of the first leg and the second member extends 360 degrees about a portion of the second leg.

9. A surgical system as recited in claim 5, wherein the first member includes a longitudinal tab configured for engagement with an outer surface of the first leg to form a friction fit connection with the first leg.

10. A surgical system as recited in claim 1, wherein the legs each include a capturing element configured for engagement with the vertebral tissue.

11. A surgical system as recited in claim 10, wherein the capturing element includes a textured gripping surface.

12. A surgical system as recited in claim 10, wherein the capturing element includes a C-shaped configuration for engagement with the vertebral tissue including laminae.

13. A surgical system as recited in claim 10, wherein the capturing element includes a bracket for engagement with the vertebral tissue including a spinous process.

14. A surgical system as recited in claim 10, wherein the capturing element includes a hook for engagement with a bone fastener engageable with the vertebral tissue.

15. A surgical system as recited in claim 10, wherein the capturing element includes a ring for engagement with a bone fastener engageable with the vertebral tissue.

16. A surgical system as recited in claim 10, wherein the capturing element includes a connector for engagement with a bone fastener engageable with the vertebral tissue.

17. A surgical system comprising:

a longitudinal element;

non-cannulated first and second legs, the legs each including an interior rail;

a first member connected with the longitudinal element and defining a first passageway extending along a first axis, the first leg being disposed within the first passageway such that a proximal end of the first leg extends through a proximal opening of the first passageway, a first projection of the first leg extends through a first opening of the first member, and a distal end of the first leg extends through a distal opening of the first passageway, the first projection extending perpendicular to the first axis; and a second member connected with the longitudinal element and defining a second passageway extending along a second axis, the second leg being disposed within the second passageway such that a proximal end of the second leg extends through a proximal opening of the second passageway, a second projection of the second leg extends through a second opening of the second member, and a distal end of the first leg extends through a distal opening of the second passageway, the second projection extending perpendicular to the second axis, the members being relatively movable between a first orientation in which the first member directly engages the second member and a second orientation in which the members are spaced apart from one another to distract and/or compress vertebral tissue, and the members each including a longitudinal groove configured for slidable engagement with one of the interior rails to form a dovetail connection and prevent rotation of the legs relative to the members.

18. A surgical system as recited in claim 17, wherein the longitudinal element includes a toothed rack.

19. A surgical system as recited in claim 17, wherein:

the first member includes a tubular arm configured for disposal of the first leg such that an inner surface of the first member that defines the first passageway engages an outer surface of the first leg;

and the second member includes a tubular arm configured for disposal of the second leg such that an inner surface of the second member that defines the second passageway engages an outer surface of the second leg.

20. A surgical system comprising:

non-cannulated first and second legs, the legs each including an engaging surface and an interior rail;

a first member connectable with the engaging surface of the first leg, the first member defining a first passageway extending along a first axis, the first leg being disposed within the first passageway such that a proximal end of the first leg extends through a proximal opening of the first passageway, a first projection of the first leg extends through a first opening of the first member, and a distal end of the first leg extends through a distal opening of the first passageway, the first projection extending perpendicular to the first axis;

a second member connectable with the engaging surface of the second leg, the second member defining a second passageway extending along a second axis, the second leg being disposed within the second passageway such that a proximal end of the second leg extends through a proximal opening of the second passageway, a second projection of the second leg extends through a second opening of the second member, and a distal end of the first leg extends through a distal opening of the second passageway, the second projection extending perpendicular to the second axis;

wherein legs are selected for connection with the members such that the members are relatively movable between a first orientation in which the first member directly engages the second member and a second orientation in which the members are spaced apart from one another to distract and/or compress vertebral tissue, and wherein the members each include a longitudinal groove configured for slidable engagement with one of the interior rails to form a dovetail connection and prevent rotation of the legs relative to the members.

* * * * *